United States Patent
Castro Pineiro et al.

(10) Patent No.: US 6,756,511 B2
(45) Date of Patent: Jun. 29, 2004

(54) GAMMA-SECRETASE INHIBITORS

(75) Inventors: Jose Luis Castro Pineiro, Bishops Stortford (GB); Timothy Harrison, Great Dunmow (GB); Peter Alan Hunt, Saffron Walden (GB); Alan John Nadin, Sawbridgeworth (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 6 days.

(21) Appl. No.: 10/181,871

(22) PCT Filed: Jan. 19, 2001

(86) PCT No.: PCT/GB01/00200

§ 371 (c)(1),
(2), (4) Date: Jul. 18, 2002

(87) PCT Pub. No.: WO01/53255

PCT Pub. Date: Jul. 26, 2001

(65) Prior Publication Data

US 2003/0114387 A1 Jun. 19, 2003

(30) Foreign Application Priority Data

Jan. 24, 2000 (GB) .............................................. 0001589
Feb. 17, 2000 (GB) .............................................. 0003767

(51) Int. Cl.$^7$ .................... C07C 233/05; A61K 31/165
(52) U.S. Cl. ......................... 564/153; 560/27; 560/29; 540/509; 540/510; 514/484; 514/485; 514/616; 514/221
(58) Field of Search ................................. 514/484, 485, 514/616, 221; 564/153; 560/27, 29; 540/509, 510

(56) References Cited

U.S. PATENT DOCUMENTS 5,703,129 A  12/1997  Felsenstein et al.

6,545,127 B1 * 4/2003  Tang et al. .................. 530/350

FOREIGN PATENT DOCUMENTS

| EP | 0337714 | 4/1989 |
| EP | 0356223 | 8/1989 |
| EP | 0 778 266 | 6/1997 |
| WO | WO 98/15828 | 4/1998 |

OTHER PUBLICATIONS

Price and Sisodia, Annu. Rev. Neurosci., 1998, 21:479–505.

Selkoe, J. Biol. Chem., 271(31), 18295–18298, 1996.

Steiner et al, J. Biol. Chem., 274(12), 7615–7618, 1999.

Konvalinka et al., Eur. J. Biocheom., vol. 250, pp. 559–566 (1997).

Shearman et al., Biochemistry, vol. 39, No. 30, pp. 8698–8704 (Jul. 6, 2000).

* cited by examiner

Primary Examiner—Shailendra Kumar
(74) Attorney, Agent, or Firm—John C. Todaro; Melvin Winokur

(57) ABSTRACT

Gamma-secretase inhibitors, useful in the treatment or prevention of Alzheimer's disease, are disclosed. The preferred compounds have, as the central portion of the molecule, the structure (a) and are di-astereoisomers of known protease inhibitors.

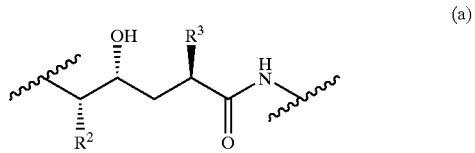

9 Claims, No Drawings

GAMMA-SECRETASE INHIBITORS

CROSS REFERENCE TO RELATED APPLICATIONS

This application is a U.S. National Phase application under 35 U.S.C. §371 of PCT Application No. PCT/GB01/00200, filed Jan. 19, 2001, which claims priority under 35 U.S.C. §119 from GB Application No. 0001589.1, filed Jan. 24, 2000, and from GB Application No. 0003767.1, filed Feb. 17, 2000.

The present invention relates to compounds, their salts, pharmaceutical compositions comprising them, processes for making them and their use in treating Alzheimer's Disease.

Alzheimer's Disease (AD) is characterised by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The ragged $NH_2$- and COOH-termini of the native Aβ amyloid indicates that a complex mechanism of proteolysis is involved in its biogenesis.

The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβ domain (between residues $Lys^{16}$ and $Leu^{17}$) to release α-$APP_s$ and precludes the release of intact Aβ. A minor portion of $APP_s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity(γ-secretase) exists under normal conditions which can generate the COOH-terminus of Aβ.

It is believed that γ-secretase itself depends for its activity on the presence of presenilin-1. In a manner that is not fully understood presenilin-1 appears to undergo autocleavage.

The compounds of the present invention are useful for treating AD by inhibiting the activity of the putative γ-secretase thus preventing the formation of insoluble Aβ and arresting the production of Aβ. Further, some of the present compounds also stabilise full-length presenilin-1.

In a further aspect some of the compounds of the present application are useful as inhibitors of presenilin-1 cleavage.

The compounds of the present invention are related to HIV protease inhibitors described in EP-A-337 714 and EP-A-356 223, both in the name of Merck & Co., Inc.. These compounds are aspartyl protease inhibitors. Specifically, a subset of the compounds of the present invention differ from those previously described by the stereochemistry of a hydroxyl group which is a particularly preferred feature of the present invention and has not previously been disclosed for these particular compounds. This is a surprising feature giving rise to the present invention.

The present invention, in one aspect, provides a compound comprising the group:

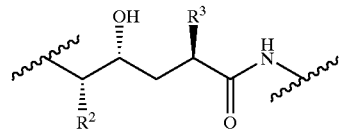

wherein $R^2$ and $R^3$ are as defined below, which compound is a diastereoisomer of a known protease inhibitor comprising the group

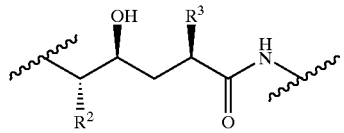

wherein $R^2$ and $R^3$ are as defined below.

The present invention accordingly provides a compound of formula I or a pharmaceutically acceptable salt thereof:

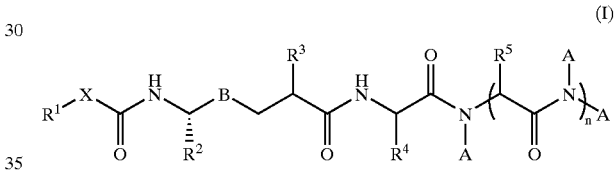

(I)

wherein:
  $R^1$ is (1) $C_{1-10}$alkyl, $C_{2-10}$alkenyl or $C_{2-10}$alkynyl optionally substituted with one to three substituents independently chosen from:
    (i) hydroxy;
    (ii) carboxy;
    (iii) halogen;
    (iv) $C_{1-4}$alkoxy;
    (v) $C_{1-4}$alkoxycarbonyl;
    (vi) —$NR^6R^7$ wherein $R^6$ and $R^7$ are independently chosen from hydrogen, $C_{1-5}$alkyl and $C_{1-5}$alkoxy$C_{1-5}$alkyl;
    (vii) —$CONR^6R^7$ or $OCONR^6R^7$ wherein $R^6$ and $R^7$ are independently as defined above;
    (viii) —$N(R^8)QR^9$ wherein:
      Q is C(O), C(S), $SO_2$ or $C(NH_2)$;
      $R^8$ is hydrogen or $C_{1-4}$alkyl; and
      $R^9$ is hydrogen, $C_{1-4}$alkyl, $C_{1-4}$alkoxy, amino, $C_{1-4}$alkylamino di($C_{1-4}$alkyl)amino wherein each alkyl group is independently chosen;
    (ix) $C_{3-7}$cycloalkyl;
    (x) phenyl or naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; each of which is optionally substituted by one to three groups independently chosen from:
      (a) halogen, cyano and nitro,
      (b) hydroxy,
      (c) $C_{1-4}$alkyl, $C_{2-4}$alkenyl and $C_{2-4}$alkynyl, (d) $C_{1-4}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ is independently as defined above and $R^{8'}$ is independently as defined for $R^8$, and
(k) $NR^8SO_2R^{8'}$ wherein $R^8$ and $R^{8'}$ are independently as defined above; or (2) phenyl or naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; each of which is optionally substituted by one to three groups independently chosen from:
(a) halogen, cyano and nitro,
(b) hydroxy,
(c) $C_{1-4}$alkyl, $C_{2-4}$alkenyl and $C_{2-4}$alkynyl,
(d) $C_{1-4}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ and $R^{8'}$ are independently as defined above, and
(k) $NR^8SO_2R^{8'}$ wherein $R^8$ and $R^{8'}$ are independently as defined above;

$R^2$ and $R^3$ are independently chosen from $C_{1-10}$alkyl, $C_{1-10}$alkoxy, $C_{2-10}$alkenyl, $C_{2-10}$alkenyloxy, $C_{2-10}$alkynyl or $C_{2-10}$alkynyloxy; phenyl; naphthyl; a five-membered heteroaromatic ring containing 1, 2, 3 or 4 heteroatoms independently chosen from O, N and S, at most one of the heteroatoms being O or S; a six-membered heteroaromatic ring containing 1, 2 or 3 nitrogen atoms; and a group $(CH_2)_pQ^1$ wherein $Q^1$ is phenyl, naphthyl, a five-membered heteroaromatic ring containing 1, 2, 3 or 4 heteroatoms independently chosen from O, N and S, at most one of the heteroatoms being O or S, and a six-membered heteroaromatic ring containing 1, 2 or 3 nitrogen atoms; and wherein each of $R^2$ and $R^3$ is independently optionally substituted by one to three groups independently chosen from:
(a) halogen, cyano and nitro,
(b) hydroxy,
(c) $C_{1-3}$alkyl, $C_{2-3}$alkenyl and $C_{2-3}$alkynyl,
(d) $C_{1-3}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ and $R^{8'}$ are independently as defined above,
(k) $NR^8SO_2R^{8'}$ where $R^8$ and $R^{8'}$ are independently as defined above;

alternatively $R^3$ may be hydrogen;

$R^4$ and $R^5$ are independently chosen from hydrogen, $C_{1-6}$alkyl optionally substituted by halogen, hydroxy, thiol, amino, $C_{1-4}$alkoxy, $C_{1-4}$alkylthio, carboxy, $C_{1-4}$alkoxycarbonyl and $(CH_2)_qQ^2$ wherein $Q^2$ is a five-membered unsaturated heterocycle containing 1, 2, 3 or 4 heteroatom optionally chosen from O, N, and S providing that not more than one heteroatom is O or S, a six-membered unsaturated heterocycle containing 1, 2 or 3 N atoms and phenyl and naphthyl, or a fused ring which is indolyl, each of the foregoing rings being optionally substituted with one to three groups independently chosen from hydroxy, $C_{1-4}$alkyl, $C_{1-4}$alkoxy, thiol, $C_{1-4}$alkylthio, halogen, amino, carboxy, amido, $CO_2H$ and $—NHC(NH_2)_2$ and wherein each of the foregoing rings is optionally fused to a benzene ring; and A is:
(1) hydrogen;
(2) $C_{1-10}$alkyl, $C_{2-10}$alkenyl or $C_{2-10}$alkynyl optionally substituted with one to three substituents independently chosen from:
(i) hydroxy;
(ii) carboxy;
(iii) halogen;
(iv) $C_{1-4}$alkoxy;
(v) $C_{1-4}$alkoxycarbonyl;
(vi) $—NR^6R^7$ wherein $R^6$ and $R^7$ are independently chosen from hydrogen, $C_{1-5}$alkyl and $C_{1-5}$alkoxy$C_{1-5}$alkyl;
(vii) $—CONR^6R^7$ or $OCONR^6R^7$ wherein $R^6$ and $R^7$ are independently as defined above;
(viii) $—N(R^8)QR^9$ wherein:
Q is $C(O)$, $C(S)$, $SO_2$ or $C(NH_2)$;
$R^8$ is hydrogen or $C_{1-4}$alkyl; and
$R^9$ is hydrogen, $C_{1-4}$alkyl, $C_{1-4}$alkoxy, amino, $C_{1-4}$alkylamino di($C_{1-4}$alkyl)amino wherein each alkyl group is independently chosen;
(ix) $C_{3-7}$cycloalkyl;
(x) phenyl or naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; each of which is optionally substituted by one to three groups independently chosen from:
(a) halogen, cyano and nitro,
(b) hydroxy,
(c) $C_{1-4}$alkyl, $C_{2-4}$alkenyl and $C_{2-4}$alkynyl,
(d) $C_{1-4}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above, (j) N(R⁸)COR⁸' wherein R⁸ is independently as defined above and R⁸' is independently as defined for R⁸, and (k) NR⁸SO₂R⁸' wherein R⁸ and R⁸' are independently as defined above; or (3) a seven-membered heterocycle
having an otherwise unsubstituted carbon atom at the point of attachment to the rest of the compound of formula I,
having at a first atom alpha to the point of attachment a carbon atom which is unsubstituted or substituted by an oxygen or sulphur atom,
having at a first atom beta to the point of attachment, which atom is alpha to the foregoing first atom alpha, a carbon atom or a nitrogen atom,
having at a second atom alpha to the point of attachment a carbon atom, which is optionally substituted by oxygen, or a nitrogen atom,
having at a second atom beta to the point of attachment, which atom is alpha to the foregoing second atom alpha, a carbon atom or a nitrogen atom,
and having at the two remaining atoms carbon atoms;
a double bond may be present between the second atom alpha and the second atom beta;
the seven-membered heterocycle may be fused to one or two aromatic rings via any adjacent pair of atoms other than the point of attachment and the first atom alpha alone or in combination;
the aromatic ring may be benzene or a five-membered heterocycle containing 1, 2, 3 or 4 heteroatoms chosen from O, N and S providing that not more than one heteroatom is O or S or a six-membered heterocycle containing 1, 2 or 3 nitrogen atoms;
alternatively a pair of adjacent carbon atoms in the seven-membered heterocycle, other than the point of attachment and the first atom alpha alone or in combination, may form part of a fused cyclopropyl or cyclopentyl ring;
one to three substitutable atoms of the seven-membered heterocycle are optionally substituted by:
an aromatic ring as defined above optionally substituted by hydroxy, halogen, methoxy or alkyl having one to four carbon atoms;
an alkyl group having one to four carbon atoms optionally substituted by a halogen atom, hydroxy, an aromatic ring as defined above optionally substituted by hydroxy, halogen, methoxy or alkyl having one to four carbon atoms, cycloalkyl having three to seven carbon atoms, methoxy, bicycloalkyl having seven to twelve carbon atoms, heterocycle having five to seven atoms one of which is oxygen, nitrogen or sulphur which is optionally oxidized;
a heterocycle having five to seven atoms one of which is oxygen, nitrogen or sulphur which is optionally oxidized;
cycloalkyl having three to seven carbon atoms;
or bicycloalkyl having seven to twelve carbon atoms;
or the two groups A attached to the same nitrogen atom, together with that atom, form: a five-membered heterocyclic ring optionally containing 1, 2 or 3 further heteroatoms chosen from O, N and S, not more than one of the heteroatoms being O or S; or a six-membered heterocyclic ring optionally containing 1 or 2 further nitrogen atoms; each of which is optionally substituted by one to three groups independently chosen from:

(a) halogen, cyano and nitro,
(b) hydroxy,
(c) $C_{1-4}$alkyl, $C_{2-4}$alkenyl and $C_{2-4}$alkynyl,
(d) $C_{1-4}$alkoxy,
(e) NR⁶R⁷ wherein R⁶ and R⁷ are independently as defined above,
(f) CO₂R⁸ wherein R⁸ is independently as defined above,
(g) CONR⁶R⁷ or OCONR⁶R⁷ wherein R⁶ and R⁷ are independently as defined above,
(h) SO₂NR⁶R⁷ wherein R⁶ and R⁷ are independently as defined above,
(i) CH₂NR⁶R⁷ wherein R⁶ and R⁷ are independently as defined above,
(j) N(R⁸)COR⁸' wherein R⁸ is independently as defined above and R⁸' is independently as defined for R⁸, and
(k) NR⁸SO₂R⁸' wherein R⁸ and R⁸' are independently as defined above;

B is C=O or CHOH in the R configuration;
X is oxygen or a bond;
n is zero or one, and
p is zero, one, two or three; and
q is zero, one, two or three;
with the proviso that no carbon atom is substituted by more than one hydroxy group.

In an embodiment the compounds of the present invention are of formula I':

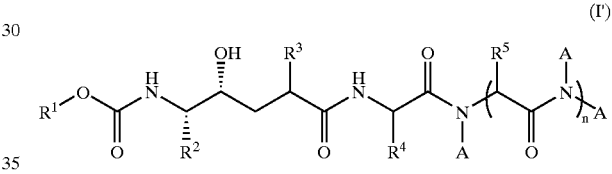

(I')

where $R^1$, $R^2$, $R^3$, $R^4$, $R^5$, A and n are as defined above.

In one embodiment the compounds of the present invention are of formula I":

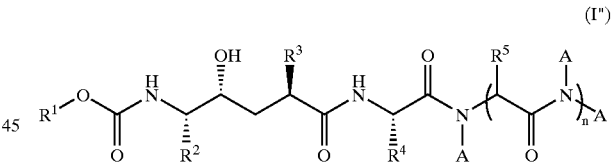

(I")

where $R^1$, $R^2$, $R^3$, $R^4$, $R^5$, A and n are as defined above.

In another embodiment there are provided compounds of formula I''':

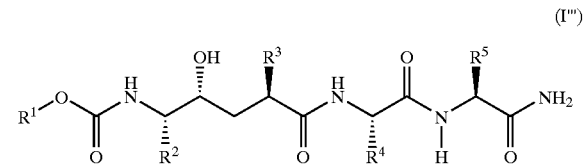

(I''')

where $R^1$, $R^2$, $R^3$, $R^4$ and $R^5$ are as defined above.

The following preferred definitions of substituents apply to each of the formulae I, I', I" and I''' which refer to those substituents.

Preferably $R^1$ is (1) $C_{1-10}$alkyl, $C_{2-10}$alkenyl or $C_{2-10}$alkynyl optionally substituted with one to three substituents independently chosen from:

(i) hydroxy;
(ii) halogen;
(iii) amino;
(iv) $C_{1-4}$alkoxy; and
(v) phenyl which is optionally substituted by one or two groups independently chosen from:
  (a) halogen, cyano and nitro,
  (b) hydroxy,
  (c) $C_{1-4}$alkyl, $C_{2-4}$alkenyl and $C_{2-4}$alkenyl,
  (d) $C_{1-4}$alkoxy and
  (e) amino; or
(2) phenyl which is optionally substituted by one or two groups independently chosen from:
  (a) halogen, cyano and nitro,
  (b) hydroxy,
  (c) $C_{1-4}$alkyl, $C_{2-4}$alkenyl and $C_{2-4}$alkynyl,
  (d) $C_{1-4}$alkoxy and
  (e) amino.

When $R^1$ is a heterocyclic ring it may be saturated, partially saturated or unsaturated. Preferably the heterocyclic ring is a heteroaromatic ring.

More preferably $R^1$ is $C_{1-10}$alkyl optionally substituted with up to three substituents as defined above. Even more preferably $R^1$ is $C_{1-6}$alkyl optionally substituted by one to three substituents as defined above. Most preferably $R^1$ is $C_{1-6}$alkyl optionally substituted by halogen, phenyl, hydroxy or $C_{1-4}$alkoxy. In particular $R^1$ may be tertiary butyl or benzyl.

$R^2$ and $R^3$ may be independently chosen from phenyl; naphthyl; a five-membered heteroaromatic ring containing 1, 2, 3 or 4 heteroatoms independently chosen from O, N and S, at most one of the heteroatoms being O or S; a six-membered heteroaromatic ring containing 1, 2 or 3 nitrogen atoms; and a group $(CH_2)_pQ^1$ wherein $Q^1$ is phenyl; naphthyl; a five-membered heteroaromatic ring containing 1, 2, 3 or 4 heteroatoms independently chosen from O, N and S, at most one of the heteroatoms being O or S; and a six-membered heteroaromatic ring containing 1, 2 or 3 nitrogen atoms; and wherein each of $R^2$ and $R^3$ is independently optionally substituted by one to three groups independently chosen from:
(a) halogen, cyano and nitro,
(b) hydroxy,
(c) $C_{1-3}$alkyl, $C_{2-3}$alkenyl and $C_{2-3}$alkynyl,
(d) $C_{1-3}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ and $R^{8'}$ are independently as defined above,
(k) $NR^8SO_2R^{8'}$ where $R^8$ and $R^{8'}$ are independently as defined above;

More preferably $R^2$ and $R^3$ are $(CH_2)_pQ^1$.
Preferably p is one.
Preferably $Q^1$ is phenyl optionally substituted by one or two groups independently chosen from:
(a) halogen, cyano and nitro,
(b) hydroxy,
(c) $C_{1-4}$alkyl, $C_{2-4}$alkenyl and $C_{2-4}$alkynyl,
(d) $C_{1-4}$alkoxy and
(e) amino.

In one embodiment $R^2$ and $R^3$ are both benzyl.
More preferably $Q^1$ is phenyl.
Preferably $R^4$ and $R^{5'}$ are independently chosen from optionally substituted $C_{1-6}$alkyl and $(CH_2)_qQ^2$. More preferably $R^4$ and $R^5$ are independently chosen from $C_{1-6}$alkyl and $(CH_2)_qQ^2$.
Preferably $Q^2$ is optionally substituted phenyl. More preferably $Q^2$ is phenyl.
In particular $R^4$ and $R^5$ are independently chosen from methyl, benzyl, phenyl, 2-methylpropyl, 1-hydroxyethyl, isopropyl and isobutyl.

A is preferably hydrogen or a group

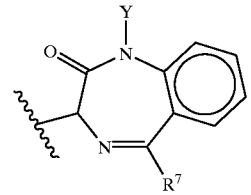

wherein $R^7$ is phenyl, $C_{1-6}$alkyl or $C_{3-7}$cycloalkyl and Y is hydrogen or $C_{1-6}$ alkyl. More preferably A is hydrogen or a group as defined above wherein $R^7$ is a cyclohexyl group.

X is preferably oxygen.
n may be zero. n may be one.
p is preferably one.
q is preferably zero or one.

Thus a subclass of compounds of formula I and I' is provided wherein:
$R^1$ is
(1) $C_{1-10}$alkyl, $C_{2-10}$alkenyl or $C_{2-10}$alkynyl optionally substituted with one or more substituents independently chosen from:
  (i) hydroxy;
  (ii) halogen;
  (iii) amino;
  (iv) $C_{1-4}$alkoxy; and
  (v) phenyl which is optionally substituted by one or two groups independently chosen from:
    (a) halogen, cyano and nitro,
    (b) hydroxy,
    (c) $C_{1-4}$alkyl, $C_{2-4}$alkenyl and $C_{2-4}$alkynyl,
    (d) $C_{1-4}$alkoxy and
    (e) amino; or
(2) phenyl which is optionally substituted by one or two groups independently chosen from:
  (a) halogen, cyano and nitro,
  (b) hydroxy,
  (c) $C_{1-4}$alkyl, $C_{2-4}$alkenyl and $C_{2-4}$alkynyl,
  (d) $C_{1-4}$ alkoxy and
  (e) amino;
$R^2$ and $R^3$ are both $(CH_2)_pQ^1$ wherein $Q^1$ is phenyl optionally substituted by one or two groups independently chosen from:
  (a) halogen,
  (b) hydroxy,
  (c) $C_{1-4}$alkyl, $C_{2-4}$alkenyl and $C_{2-4}$alkynyl,
  (d) $C_{1-4}$alkoxy and
  (e) amino;
$R^4$ and $R^5$ are independently chosen from $C_{1-6}$alkyl optionally substituted by halogen, hydroxy, amino or $C_{1-4}$alkoxy and $(CH_2)_qQ^2$ wherein $Q^2$ is phenyl optionally substituted by hydroxy, $C_{1-4}$alkyl, $C_{1-4}$alkoxy, thiol, $C_{1-4}$alkylthio, halogen, amino, carboxy, amido, $CO_2H$ and —$NHC(NH_2)_2$;

A is hydrogen or

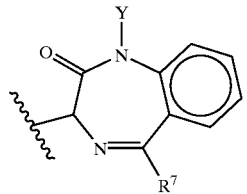

wherein $R^7$ is phenyl, $C_{1-6}$alkyl or $C_{3-7}$cycloalkyl;

Y is hydrogen or $C_{1-6}$ alkyl;

n is zero or one;

p is one; and q is zero or one.

For the avoidance of doubt each time the moieties A, $R^6$, $R^7$, $R^8$, $R^{8'}$ and $R^9$ occur more than once in the definition of the compounds of formula (I) they are chosen independently.

As used herein, the expression "$C_{1-10}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{1-6}$alkyl", "$C_{1-4}$alkyl", "$C_{2-10}$alkenyl", "$C_{2-4}$alkenyl", "$C_{2-10}$ alkynyl" and "$C_{2-4}$alkynyl" are to be construed in an analogous manner.

The expression "$C_{3-7}$cycloalkyl" as used herein includes cyclic propyl, butyl, pentyl, hexyl and heptyl groups such as cyclopropyl and cyclohexyl.

The term "heterocyclic" includes rings which are saturated, partially saturated or unsaturated. Unsaturated heterocyclic rings are also known as heteroaromatic rings.

Suitable 5- and 6-membered heteroaromatic rings include pyridinyl, pyridazinyl, pyrimidinyl, pyrazinyl, pyrrolyl, pyrazolyl, oxazolyl, isoxazolyl, thiazolyl, isothiazolyl, imidazolyl, oxadiazolyl and thiadiazolyl groups. A suitable 5-membered heteroaromatic ring containing four nitrogen atoms is tetrazolyl. Suitable 6-membered heteroaromatic rings containing three nitrogen atoms include 1,2,4-triazine and 1,3,5-triazine. Suitable saturated heterocyclic rings include piperazine, morpholine, piperidine, tetrahydrofuran and tetrahydrothiophene. Tetrahydrofuran is preferred.

The term "halogen" as used herein includes fluorine, chlorine, bromine and iodine, of which fluorine and chlorine are preferred.

As used herein the term "$C_{1-4}$alkoxy" includes methoxy and ethoxy groups, and straight-chained, branched and cyclic propoxy and butoxy groups, including cyclopropylmethoxy.

Specific Examples according to the present invention include:

{1S-benzyl-4R-[1-(1S-carbamoyl-2-(R)-hydroxypropylcarbamoyl)-(S)-ethylcarbamoyl]-2R-hydroxy-5-phenylpentyl}-carbamic acid, tert-butyl ester;

{1S-benzyl-4R-[1-(1S-carbamoyl-2-(S)-methylbutylcarbamoyl)-1S-2-methylpropylcarbamoyl]-2R-hydroxy-5-phenylpentyl}carbamic acid tert-butyl ester;

{1S-benzyl-4-[1-(5-cyclohexyl-2-oxo-2,3-dihydro-1H-benzo[e][1,4]diazepin-3(R,S)-yclarbamoyl)-(S)-ethylcarbamoyl]-2R-hydroxybutyl}-carbamic acid, tert-butyl ester;

{1S-benzyl-4R-[1-(5-cyclohexyl-2-oxo-2,3-dihydro-1H-benzo[e][1,4]diazepin-3(R,S)-yclarbamoyl)-(S)-ethylcarbamoyl]-2R-hydroxy-5-phenylpentyl}-carbamic acid, tert-butyl ester;

{1S-benzyl-4R-[1-(1S-carbamoyl-2-phenylethylcarbamoyl)-1S-3-methylbutylcarbamoyl]-2R-hydroxy-5-phenylpentyl}-carbamic acid, benzyl ester;

{1S-benzyl-4R-[1-(1S-carbamoyl-2-phenylethylcarbamoyl)-1S-3-methylbutylcarbamoyl]-2-oxo-5-phenylpentyl}-carbamic acid tert-butyl ester;

{1S-benzyl-4R-[1-(1S-carbamoyl-2-phenylethylcarbamoyl)-1S-3-methylbutylcarbamoyl]-2R-hydroxy-5-phenylpentyl}carbamic acid tert-butyl ester;

{1S-benzyl-4R-[1-(1S-carbamoyl-2-phenylethylcarbamoyl)-S-ethylcarbamoyl]-2R-hydroxy-5-phenylpentyl}carbamic acid tert-butyl ester;

(1S-benzyl-4R-{1S-[(carbamoylphenylmethyl)carbamoyl]-S-ethylcarbamoyl}-2R-hydroxy-5-phenylpentyl)carbamic acid tert-butyl ester; and the pharmaceutically acceptable salts thereof.

Examples of pharmaceutically acceptable salts are hydrochlorides, sulfates, citrates, tartrates, acetates, methanesulfonates, phosphates, oxalates and benzoates.

The compounds of the present invention have an activity as inhibitors of γ secretase. In a preferred embodiment the compounds of the invention inhibit proteolysis of PS-1.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycel, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

For treating or preventing Alzheimer's Disease, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

There is also provided a process for producing a compound of formula I or a pharmaceutically acceptable salt thereof which comprises reacting a compound of formula II with a compound of formula III:

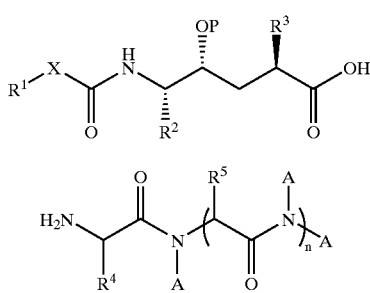

wherein $R^1$, $R^2$, $R^3$, $R^4$, $R^5$, A, X and n are as defined above and P is hydrogen or a protecting group such as a trialkylsilane group, for example t-butyl dimethylsilyl, followed, if necessary, by deprotection of the resulting compound to produce a compound of formula I. The reaction is generally carried out in the presence of coupling agents such as 1-(3-dimethylaminopropyl)-3-ethylcarbodiimide hydrochloride and 1-hydroxybenzotriazole in a solvent such as DMF, generally at about room temperature for six to twelve hours. Any necessary deprotection is achieved by conventional means.

The compound of formula II is produced by reacting a compound of formula IV:

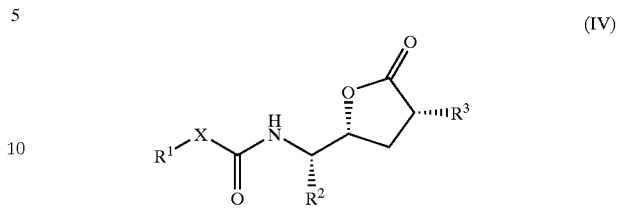

wherein $R^1$, $R^2$, $R^3$ and X are as defined above in a solvent such as dioxane, with a base such as lithium hydroxide in a polar solvent such as water generally at room temperature for above five hours. If desired the resulting compound of formula II in which P is hydrogen is protected by conventional means.

The compound of formula IV is produced by reacting a compound of formula V with a compound of formula VI or a compound of formula VII:

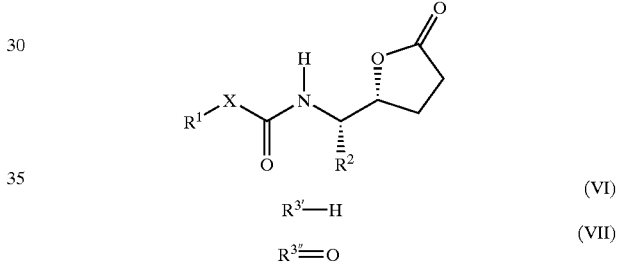

wherein $R^1$, $R^2$ and X are as defined above, $R^{3'}$ is the acyl derivative of a group $R^3$ as defined above and $R^{3''}$ is a group $R^3$ bound to an oxo group at the portion of $R^3$ which connects to the compound of formula V. The reaction is generally carried out in the presence of a base such as lithium diisopropylamide in a solvent such as THF generally cooled to −78° C. for about thirty minutes. The reaction mixture is subsequently dehydrated without purification and then hydrogenated with, for example, hydrogen over 5% Pd/C catalyst at about 50 psi for about 2 h.

The compound of formula V in which $R^1$ is tertiary butyl and $R^2$ is benzyl can be prepared as described by J. Litera et al., Collect. Czech. Chem. Commun. 1998, 63, 231ff. Compounds of formula V in which $R^1$ is other than tertiary butyl and $R^2$ is other than benzyl can be made by analogous methods.

Compounds of formulae III and VI are commercially available or known in the prior art or can be made from commercially available or known compounds by standard methods.

Alternatively the compounds of the present invention can be made by the following typical experimental procedure or by methods analogous thereto:

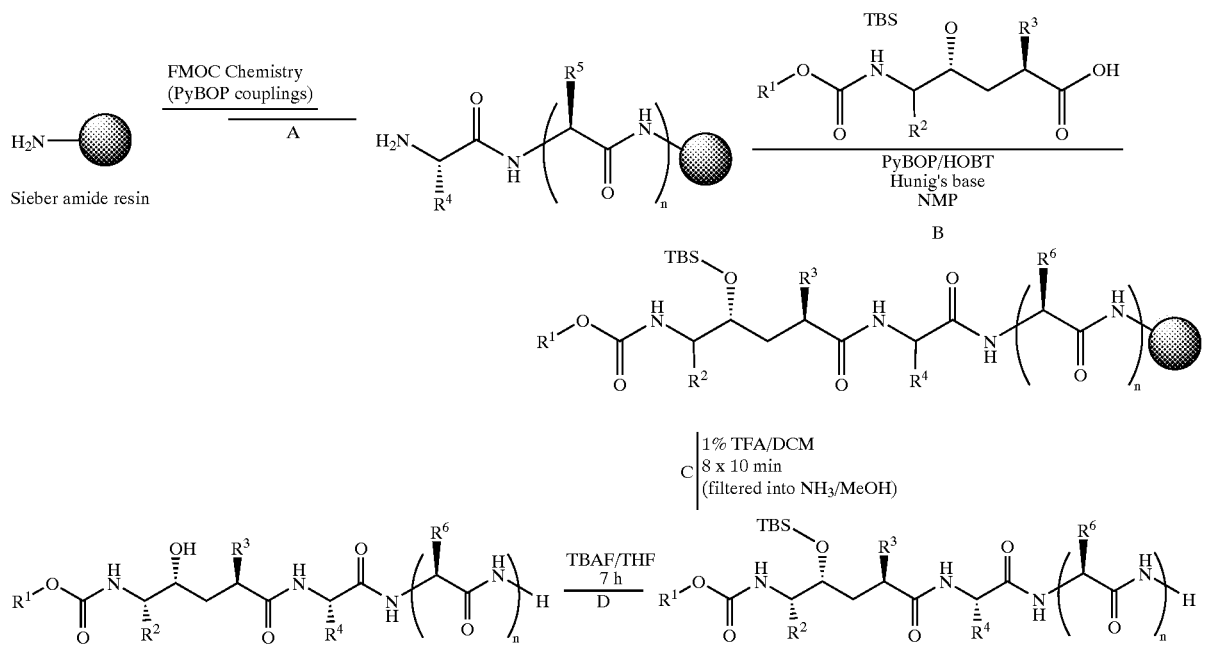

in which $R^1$, $R^2$, $R^3$, $R^4$, $R^5$ and n are as defined above and A is hydrogen.

A. 50 mg (0.030 mmol) of FMOC-Sieber amide resin is placed in a Quest 210 solid phase reactor and treated with Piperidine/DMF (0.5 mL; 1:1 mixture) with mixing for 30 minutes. The reactor is drained and washed with DMA (10×1 mL). 1 mL of a 0.1 M solution of FMOC-amino acid 1 in DMA is added followed by 0.2 mL of a DMA mixed solution of HOBT and Hunig's base (0.5 M in both) and 0.5 mL of a 0.2 M solution of PyBOP in DMA. The reactor is mixed for 60 minutes, drained, and washed with DMA (10×1 mL). The reactor is treated with Piperidine/DMF (0.5 mL; 1:1 mixture) and mixed for 30 minutes. The reactor is drained and washed with DMA (10×1 ML). 1 mL. of a 0.1 M solution of FMOC-amino acid 2 in DMA is added followed by 0.2 mL of a DMA mixed solution of HOBT and Hunig's base (0.5 M in both) and 0.5 mL of a 0.2 M solution of PyBOP in DMA. The reactor is mixed for 60 minutes, drained, and washed with DMA (10×1 mL). The reactor is treated with Piperidine/DMF (0.5 mL; 1:1 mixture) and mixed for 30 minutes. The reactor is drained and washed with DMA (10×1 mL).

B. 21 mg (0.04 mmol) of the TBS-protected isostere and 5 mg HOBT in 0.5 mL NMP is added to the reactor, followed by Hunig's base (50 μL) and 0.5 M PyBOP in NMP (0.5 mL). The reactor is mixed for 16 h, filtered, and washed with DMA (5×1 mL), MeOH (2×1 mL) and DCE (10×1 mL).

C. The reactor is treated with 0.5 mL of a 1% solution of TFA in DCM and stood for 10 minutes. The reactor is drained into a test tube containing 2 M $NH_3$ in MeOH (1 mL) and the cleavage repeated a further 5 times (identical conditions). The product is concentrated (SpeedVac), dissolved in 1 mL DCM and washed with water (1 mL) using a phase separation CombiTube. The DCM layer is concentrated (SpeedVac) to give essentially pure TBS-protected product.

D. The product is dissolved in 1 M TBAF in THF (0.5 mL), stood for 7 h, water (2 mL) is added and the product is extracted out with DCM (3×1 mL). The product is purified by flash chromatography (5%MeOH/DCM).

All products are analyzed by analytical LC-MS utilizing diode array detection (210–250 nm) and APcI detection (150–850 amu) using a full 5%→95% MeCN gradient with 0.1% aqueous TFA. A strong M+$Na^+$ peak is oberved in the mass spectrum.

It will be understood that any compound of formula I initially obtained from the above process may, where appropriate, subsequently be elaborated into a further compound of formula I by techniques known from the art.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

A typical assay which can be used to determine the level of activity of compounds of the present invention is as follows:

(1) Mouse neuroblastoma neuro 2a cells expressing human app695 are cultured at 50–70% confluency in the presence of sterile 10 mM sodium butyrate.

(2) Cells are placed in 96-well plates at 30,000/well/100 μL in minimal essential medium (MEM) (phenol redfree) +10% foetal bovine serum (FBS), 50 mM HEPES buffer (pH7.3), 1% glutamine, 0.2 mg/mL G418 antibiotic, 10 mM sodium butyrate.

(3) Make dilutions of the compound plate. Dilute stock solution to 5.5% DMSO/110 μM compound. Mfix compounds vigorously and store at 4° C. until use.

(4) Add 10 μL compound/well. Mix plate briefly, and leave for 18 h in 37° C. incubator.

(5) Remove 90 μL of culture supernatant and dilute 1:1 with ice-cold 25 mM HEPES (pH.3), 0.1% BSA, 1.0 mM EDTA (+broad spectrum protease inhibitor cocktail; pre-aliquotted into a 96-well plate). Mix and keep on ice or freeze at −80° C.

(6) Add back 100 μL of warm MEM +10% FBS, 50 mM HEPES (pH7.3), 1% glutamine, 0.2 mg/mL G418, 10 mM sodium butyrate to each well, and return plate to 37° C. incubator.

(7) Prepare reagents necessary to determine amyloid peptide levels, for example by ELISA assay (8) To determine if compounds are cytotoxic cell viability following compound administration is assessed by the use of redox dye reduction. A typical example is a combination of redox dye MTS (Promega) and the electron coupling reagent PES. This mixture is made up according to the manufacturer's instructions and left at room temperature.

(9) Quantitate amyloid beta 40 and 42 peptides using an appropriate volume of diluted culture medium by standard ELISA techniques.

(10) Add 15 μL/well MTS/PES solution to the cells; mix and leave at 37° C.

(11) Read plate when the absorbance values are approximately 1.0 (mix briefly before reading to disperse the reduced formazan product).

The Examples of the present invention all had an $ED_{50}$ of less than 500 nM, preferably less than 200 nM and most preferably less than 100 nM in the above assay.

The following examples illustrate the present invention.

EXAMPLE 1

{1S-Benzyl-4R-[1-(1S-carbamoyl-2-(R)-hydroxypropylcarbamoyl)-(S)-ethylcarbamoyl]-2R-hydroxy-5-phenylpentyl}-carbamic acid, tert-butyl ester Step 1: [1S-(4M-Benzyl-5-oxo-tetrahydrofuran-2R-yl)-2-phenylethyl]-carbamic acid, tert-butyl ester A solution of [1S-(5-oxo-tetrahydrofuran-2R-yl)-2-phenylethyl]-carbamic acid, tert-butyl ester (prepared as described in J. Litera et al., Collect. Czech. Chem. Commun. 1998, 63, 231) (3.0 g, 0.99 mmol) in THF (10 ml) was added to a solution of lithium diisopropylamide [made from n-butyllithium (8.64 ml of a 2.5 M solution in hexane) and diisopropylamine (3.06 ml)] in THF (10 ml) at −78° C. The reaction mixture was stirred for 40 minutes at −78° C., then treated with benzaldehyde. After 30 minutes, the reaction mixture was quenched by the addition of aqueous $NH_4Cl$ (5 ml) and water. The resulting mixture was extracted with ethyl acetate and the combined extracts were washed with aqueous citric acid, aqueous $NaHCO_3$ solution and brine. The combined extracts were dried ($MgSO_4$), filtered and evaporated in vacuo to give a thick oil. This crude reaction product was treated with acetic anhydride (5 ml), triethylamine (5 ml) and heated at 120° C. for 1 h. The reaction mixture was cooled to room temperature, diluted with ether and washed with aqueous citric acid, aqueous $NaHCO_3$ solution and brine. The ethereal extracts were dried ($MgSO_4$) and evaporated in vacuo to give the reaction product as a crude solid which was used without further purification. This crude reaction product was dissolved in ethyl acetate (25 ml) and methanol (5 ml), treated with 5% Pd/C catalyst and hydrogenated at 50 psi for 2 h. The reaction mixture was filtered and evaporated in vacuo to give the title compound, which was either purified by flash column chromatography, or by trituration with ether, (yield 3.9 g, 78%). $^1$H NMR (250 MHz, $CDCl_3$) 7.38–7.15 (10H, m); 4.38–4.11 (2H, m), 3.90 (1H, brs); 3.27 (1H, dd, J=13.7, 4.0); 2.95–2.67 (4H, m), 2.28–2.17 (1H, m); 1.86–1.70 (1H, m); 1.34 (9 H, s).

Step 2: 2R-Benzyl-5S-tert-butoxycarbonylamino-4R-(tert-butyldimethylsilanyloxy)-6-phenyl-hexanoic acid The compound obtained in Step 1 (2.0 g, 5.1 mmol) was dissolved in 1,2-dimethoxyethane (36 mL) and treated with a solution of sodium hydroxide in water (1.0 M, 36 mL, 1.1 equiv.) and stirred at room temperature for 0.5 h. The reaction mixture was carefully acidified to pH 4 with citric acid, then extracted with ethyl acetate. The ethyl acetate extracts were washed with brine, dried ($MgSO_4$), filtered and evaporated in vacuo. The crude hydroxyacid was dissolved in DMF (20 mL) and treated with tert-butyldimethylsilyl chloride (7.8 g, 5 equiv.) and imidazole (4.2 g, 10 equiv.) and stirred overnight. The reaction mixture was treated with methanol and stirred for 2 h, then evaporated in vacuo. The reaction mixture was partitioned between aqueous citric acid and ethyl acetate. The organic layer was washed with brine, dried ($MgSO_4$), filtered and evaporated in vacuo. Purification by flash column chromatography gave the title compound (2.55 g, 95%) 1H NMR (400 MHz, $d_6$-DMSO) 12.08 (1H, s);7.25–7.04 (10H, m); 6.45 (1H, d, J =8.9); 3.74–3.53 (2H, m); 2.76–2.50 (5H, m); 1.8–1.5 (2H, m); 1.22 (9H, s); 0.80 (9H, s); 0.07 (3H, s); 0.05 (3H, s).

Step 3: {1S-Benzyl-4R-[1-(1S-carbamoyl-2-(R)-hydroxypropylcarbamoyl)-(S)-ethylcarbamoyl]-2R-hydroxy-5-phenylpentyl}-carbamic acid, tert-butyl ester The compound obtained in Step 2 (50 mg), $H_2N$-L-ala-L-thr-$CONH_2$ (20 mg), 1-(3-dimethylaminopropyl)-3-ethylcarbodiimide hydrochloride (22 mg) and 1-hydroxybenzotriazole (15 mg) in DMF was stirred at room temperature overnight. The reaction mixture was diluted with ethyl acetate, and the organic phase was washed with aqueous citric acid, aqueous $NaHCO_3$, brine, dried ($MgSO_4$), filtered and evaporated in vacuo. Purification by flash column chromatography gave the product (40 mg, 60%). This material was dissolved in a solution of tetrabutylammonium fluoride in THF (1.0 M, 2 ml) and stirred at room temperature overnight. The reaction mixture was diluted with citric acid and ether and the resulting precipitate was collected by filtration, washed and dried in vacuo to give the title compound. (19 mg, 57%) 1H NMR (360 MHz, $d_6$-DMSO) 8.02 (1H, d, J=6.8); 7.44 (1H, d, J =7.9); 7.26–7.08 (12H, m); 6.51 (1H, d, J=8.9); 4.89 (1H, brs); 4.67 (1H, brs); 4.27–4.23 (2H, brm); 4.04 (2H, m); 3.4 (2H, m); 2.9–2.4 (4H, m); 1.60–1.56 (2H, m); 1.24–0.99 (15H, m). In the same way as for Step 3 using the appropriate amine the following compounds were also made:

EXAMPLE 2

{1S-Benzyl-4R-[1-(1S-carbamoyl-2-(S)-methylbutylcarbamoyl)-1S-2-methylpropylcarbamoyl]-2R-hydroxy-5-phenylpentyl}-carbamic acid, tert-butyl ester $^1$H NMR (360 MHz, $d_6$-DMSO) 7.53 (1H, d, J =8.7); 7.42 (1H, d, J =8.7); 7.23–7.10 (12H, m); 6.2 (1H, vbrs); 4.48 (1H, brs); 4.19–4.09 (2H, m); 3.56–3.52 (2H, m); 2.91–2.54 (5H, m); 2.00–1.95 (1H, m); 1.74–1.61 (3H, m); 1.46–0.80 (23H, m).

EXAMPLE 3

{1S-Benzyl-4-[1-(5-cyclohexyl-2-oxo-2,3-dihydro-1H-benzo[e][1,4]diazepin-3(R,S)-ylcarbamoyl)-(S)-ethylcarbamoyl]-2R-hydroxybutyl}-carbamic acid, tert-butyl ester $^1$H NMR (400 MHz, d$_6$-DMSO) 10.63 (0.5H, s); 10.58 (0.5H, s); 8.78 (0.5 H, d, J=8.2); 8.68 (0.5H, d, J=8.2); 7.96 (1H, m); 7.73 (1H, m); 7.55–7.51 (1H, m); 7.28–7.12 (7H, m); 6.53–6.51 (1H, m); 5.03–5.00 (1H, m); 4.77–4.75 (1H, m); 4.50–4.46 (1H, m); 3.50–3.40 (1H, m); 3.00–2.85 (2H, m); 2.40–0.80 (28H, m).

EXAMPLE 4

{1S-Benzyl-4R-[1-(5-cyclohexyl-2-oxo-2,3-dihydro-1H-benzo[e][1,4]diazepin-3 3(R,S)-ylcarbamoyl)-(S)-ethylcarbamoyl]-2R-hydroxy-5-phenylpentyl}-carbamic acid, tert-butyl ester $^1$H NMR (400 MHz, d$^6$-DMSO) 10.65 (0.5H, s); 10.60 (0.5H, s); 8.62 (0.5 H, d, J=8.2); 8.53 (0.5H, d, J=7.8); 7.92–7.88 (1H, m); 7.76–7.74 (1H, m); 7.54–7.51 (1H, m); 7.29–7.09 (12H, m); 6.52–6.48 (1H, m); 5.00–4.98 (1 H, m); 4.65–4.60 (1H, m); 4.50–4.40 (1H, m); 3.51–3.38 (2H, m); 3.0–2.4 (5 H, m); 2.0–1.1 (25H, m).

EXAMPLE 5

{1S-Benzyl-4R-[1-(1S-carbamoyl-2-phenylethylcarbamoyl)-1S-3-methylbutylcarbamoyl]-2R-hydroxy-5-phenylpentyl}-carbamic acid, benzyl ester 7.89 (1H, d, J=7.2); 7.65 (1H, d, J=7.2); 7.35–7.02 (23H, m); 4.98–4.78 (3H, m); 4.44–4.37 (1H, m); 4.22–4.10 (1H, m); 3.60–3.52 (1H, m); 3.52–3.42 (1H, m); 3.02–2.98 (1H, m); 2.90–2.40 (6H, m); 1.70–1.20 (5H, m); 0.81 (3H, d, J=6.5); 0.75 (3H, d, J=6.5).

EXAMPLE 6

{1S-Benzyl-4R-[1-(1S-carbamoyl-2-phenylethylcarbamoyl)-1S-3-methylbutylcarbamoyl]-2-oxo-5-phenylpentyl}-carbamic acid tert-butyl ester {1S-benzyl-4R-[1-(1S-carbamoyl-2-phenylethylcarbamoyl)-1S-3-methylbutylcarbamoyl]-2S-hydroxy-5-phenylpentyl}-carbamic acid tert-butyl ester (S. J. deSolms et al, *J. Med. Chem.*, 1991, 34, 2852)(68.9 mg, 0.10 mmol) was dissolved in glacial acetic acid (3 mL) and treated with pyridinium dichromate (92 mg, 0.25 mmol) and stirred for 3 h at room temperature. The reaction mixture was carefully neutralized with NaHCO3 solution and extracted with ethyl acetate. The combined organic extracts were washed with NaHCO3 solution, dried (MgSO4), filtered and evaporated in vacuo. Trituration with ethyl acetate gave the title compound, (49.6 mg, 72%).

The following three compounds were made by methods described herein using FMOC-Sieber amide resin:

EXAMPLE 7

{1S-Benzyl-4R-[1-(1S-carbamoyl-2-phenylethylcarbamoyl)-1S-3-methyl-butylcarbamoyl]-2R-hydroxy-5-phenylpentyl}-carbamic acid tert-butyl ester $^1$H NMR (d$_6$-DMSO, 360 MHz) δ7.88 (1H, d, J=8 Hz), 7.63 (1H, d, J=8 Hz), 7.28–7.06 (17H, m), 6.47 (1H, d, J=9.3 Hz), 4.71 (1H, d, J=5.3 Hz), 4.40 (1H, m), 4.16 (1H, m), 3.50–2.30 (7H, m), 1.70–1.30 (5H, m), 1.24 (9H, s), 1.10 (1H, s), 0.82 (3H, d, J=6.6 Hz), 0.76 (3H, d, J=6.6 Hz). LC-MS (APcI) 673 (M+H$^+$), 695 (M+Na$^+$).

EXAMPLE 8

{1S-Benzyl-4R-[1-(1S-carbamoyl-2-phenylethylcarbamoyl)-S-ethylcarbamoyl]-2R-hydroxy-5-phenylpentyl}carbamic acid tert-butyl ester $^1$H NMR (d$_6$-DMSO, 360 MHz) δ 7.90 (1H, d, J=8 Hz), 7.66 (1H, d, J=8 Hz), 7.28–7.06 (17H, m), 6.49 (1H, d, J=9.3 Hz), 4.82 (1H, d, J=5.3 Hz), 4.43 (1H, m), 4.18 (1H, m), 3.50–2.30 (7H, m), 1.70–0.90 (15H, m). LC-MS (APcI) 631 (M+H$^+$), 653 (M+Na$^+$).

EXAMPLE 9

(1S-Benzyl-4R-{1S-[(-carbamoylphenylmethyl)carbamoyl]-S-ethylcarbamoyl}-2R-hydroxy-5-phenylpentyl)carbamic acid tert-butyl ester $^1$H NMR (d6-DMSO, 360 MHz) δ 8.11 (1H, d, J=8 Hz), 7.74 (1H, d, J=8 Hz), 7.28–7.06 (17H, m), 6.45 (1H, d, J=9.3 Hz), 4.75 (1H, d, J=5.3 Hz), 4.41 (1H, m), 4.17 (1H, m), 3.50–2.30 (5H, m), 1.70–0.90 (15H, m). LC-MS (APcI) 617 (M+H$^+$), 639 (M+Na$^+$).

For the avoidance of doubt the structures of the specific Examples of the present invention are as follows. In the case of ambiguity in the names given herein the structures below are to be taken as correct.

| Structure | Example Number |
|---|---|
| 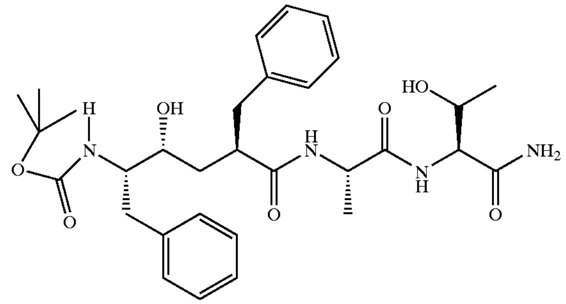 | Example 1 |

-continued
| Structure | Example Number |
|---|---|
| 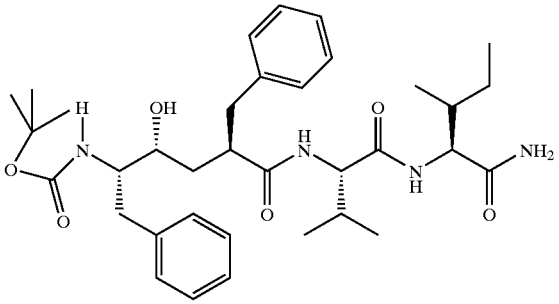 | Example 2 |
| 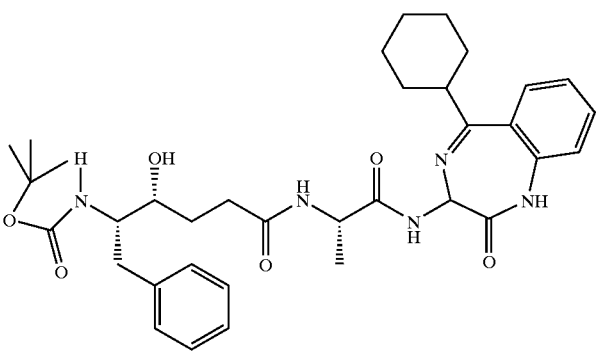 | Example 3 |
| 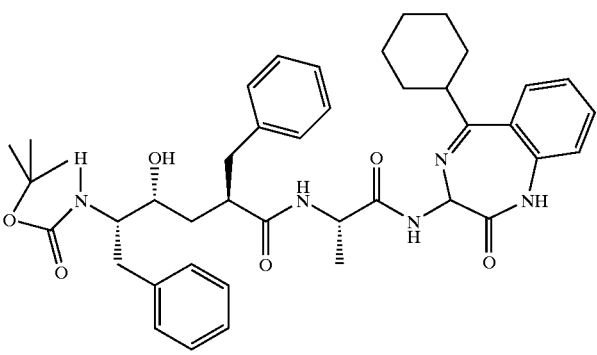 | Example 4 |
| 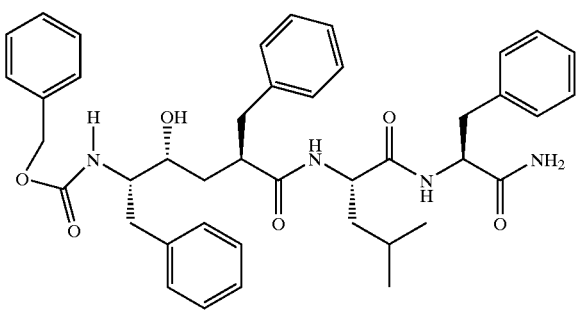 | Example 5 |

-continued
| Structure | Example Number |
|---|---|
| 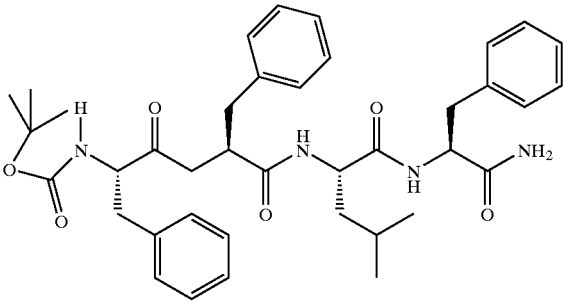 | Example 6 |
| 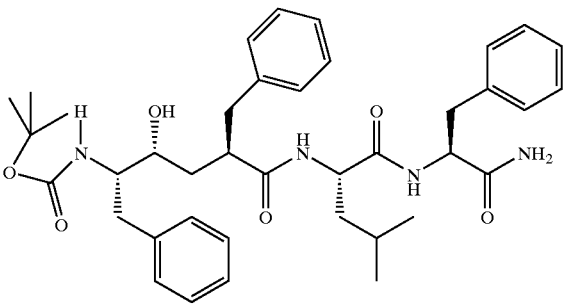 | Example 7 |
| 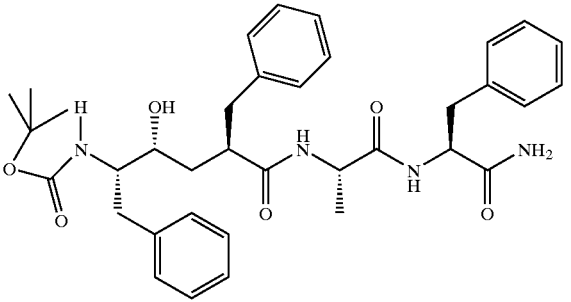 | Example 8 |
| 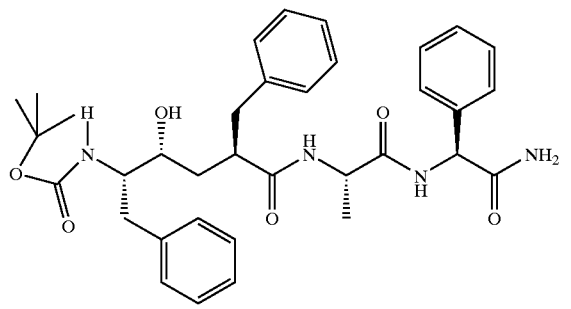 | Example 9 |

What is claimed is:
1. A compound of Formula I or a pharmaceutically acceptable salt thereof:

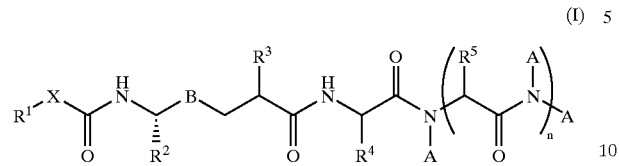

wherein:
$R^1$ is (1) $C_{1-10}$alkyl, $C_{2-10}$alkenyl or $C_{2-10}$alkynyl optionally substituted with one to three substituents independently chosen from:
(i) hydroxy;
(ii) carboxy;
(iii) halogen;
(iv) $C_{1-4}$alkoxy;
(v) $C_{1-4}$alkoxycarbonyl;
(vi) —$NR^6R^7$ wherein $R^6$ and $R^7$ are independently chosen from hydrogen, $C_{1-5}$alkyl and $C_{1-5}$alkoxy$C_{1-5}$alkyl;
(vii) —$CONR^6R^7$ or $OCONR^6R^7$ wherein $R^6$ and $R^7$ are independently as defined above;
(viii) —$N(R^8)QR^9$ wherein:
Q is $C(O)$, $C(S)$, $SO_2$ or $C(NH_2)$;
$R^8$ is hydrogen or $C_{1-4}$alkyl; and
$R^9$ is hydrogen, $C_{1-4}$alkyl, $C_{1-4}$alkoxy, amino, $C_{1-4}$alkylamino di($C_{1-4}$alkyl)amino wherein each alkyl group is independently chosen;
(ix) $C_{3-7}$cycloalkyl;
(x) phenyl or naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; each of which is optionally substituted by one to three groups independently chosen from:
(a) halogen, cyano and nitro,
(b) hydroxy,
(c) $C_{1-4}$alkyl, $C_{2-4}$alkenyl and $C_{2-4}$alkynyl,
(d) $C_{1-4}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ is independently as defined above and $R^{8'}$ is independently as defined for $R^8$, and
(k) $NR^8SO_2R^{8'}$ wherein $R^8$ and $R^{8'}$ are independently as defined above; or
(2) phenyl or naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; each of which is optionally substituted by one to three groups independently chosen from:
(a) halogen, cyano and nitro,
(b) hydroxy,
(c) $C_{1-4}$alkyl, $C_{2-4}$alkenyl and $C_{2-4}$alkynyl,
(d) $C_{1-4}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ and $R^{8'}$ are independently as defined above, and
(k) $NR^8SO_2R^{8'}$ wherein $R^8$ and $R^{8'}$ are independently as defined above;
$R^2$ and $R^3$ are independently selected from $C_{1-10}$alkyl, $C_{1-10}$alkoxy, $C_{2-10}$alkenyl, $C_{2-10}$alkenyloxy, $C_{2-10}$alkynyl or $C_{2-10}$alkynyloxy; phenyl; naphthyl; a five-membered heteroaromatic ring containing 1, 2, 3 or 4 heteroatoms independently chosen from O, N and S, at most one of the heteroatoms being O or S; a six-membered heteroaromatic ring containing 1, 2 or 3 nitrogen atoms; and a group $(CH_2)_pQ^1$ wherein $Q^1$ is phenyl, naphthyl, a five-membered heteroaromatic ring containing 1, 2, 3 or 4 heteroatoms independently chosen from O, N and S, at most one of the heteroatoms being O or S, and a six-membered heteroaromatic ring containing 1, 2 or 3 nitrogen atoms; and wherein each of $R^2$ and $R^3$ is independently optionally substituted by one to three groups independently chosen from:
(a) halogen, cyano and nitro,
(b) hydroxy,
(c) $C_{1-3}$alkyl, $C_{2-3}$alkenyl and $C_{2-3}$alkynyl,
(d) $C_{1-3}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ and $R^{8'}$ are independently as defined above,
(k) $NR^8SO_2R^{8'}$ wherein $R^8$ and $R^{8'}$ are independently as defined above;
alternatively $R^3$ may be hydrogen;
$R^4$ and $R^5$ are independently chosen from hydrogen, $C_{1-6}$alkyl, optionally substituted by halogen, hydroxy, thiol, amino, $C_{1-4}$alkoxy, $C_{1-4}$alkylthio, carboxy, $C_{1-4}$alkoxycarbonyl and $(CH_2)_qQ^2$ wherein $Q^2$ is a five-membered unsaturated heterocycle containing 1, 2, 3 or 4 heteroatom optionally chosen from O, N, and S providing that not more than one heteroatom is O or S, a six-membered unsaturated heterocycle containing 1, 2 or 3 N atoms and phenyl and naphthyl, or a fused ring which is indolyl, each of the foregoing rings being optionally substituted with one to three groups independently chosen from hydroxy, $C_{1-4}$alkyl, $C_{1-4}$alkoxy, thiol, $C_{1-4}$alkylthio, halogen, amino, carboxy, amido, $CO_2H$ and —$NHC(NH_2)_2$ and wherein each of the foregoing rings is optionally fused to a benzene ring; and A is:
  (1) hydrogen
  (2) $C_{1-10}$alkyl, $C_{2-10}$alkenyl or $C_{2-10}$alkynyl optionally substituted with one to three substituents independently chosen from:
    (i) hydroxy;
    (ii) carboxy;
    (iii) halogen;
    (iv) $C_{1-4}$alkoxy;
    (v) $C_{1-4}$alkoxycarbonyl;
    (vi) —$NR^6R^7$ wherein $R^6$ and $R^7$ are independently chosen from hydrogen, $C_{1-5}$alkyl and $C_{1-5}$alkoxy$C_{1-5}$alkyl;
    (vii) —$CONR^6R^7$ or $OCONR^6R^7$ wherein $R^6$ and $R^7$ are independently as defined above;
    (viii) —$N(R^8)QR^9$ wherein:
      Q is C(O), C(S), $SO_2$ or $C(NH_2)$;
      $R^8$ is hydrogen or $C_{1-4}$alkyl; and
      $R^9$ is hydrogen, $C_{1-4}$alkyl, $C_{1-4}$alkoxy, amino, $C_{1-4}$alkylamino di($C_{1-4}$alkyl)amino wherein each alkyl group is independently chosen;
    (ix) $C_{3-7}$cycloalkyl;
    (x) phenyl or naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; each of which is optionally substituted by one to three groups independently chosen from:
      (a) halogen, cyano and nitro,
      (b) hydroxy,
      (c) $C_{1-4}$alkyl, $C_{2-4}$alkenyl and $C_{2-4}$alkynyl,
      (d) $C_{1-4}$alkoxy,
      (e) $NR^6R^7$ wherein $R^6$ and $R^7$ are independently as defined above,
      (f) $CO_2R^8$ wherein $R^8$ is independently as defined above,
      (g) $CONR^6R^7$ or $OCONR^6R^7$ wherein $R^6$ and $R^7$ are independently as defined above,
      (h) $SO_2NR^6R^7$ wherein $R^6$ and $R^7$ are independently as defined above,
      (i) $CH_2NR^6R^7$ wherein $R^6$ and $R^7$ are independently as defined above,
      (j) $N(R^8)COR^{8'}$ wherein $R^8$ is independently as defined above and $R^{8'}$ is independently as defined for $R^8$, and
      (k) $NR^8SO_2R^{8'}$ wherein $R^8$ and $R^{8'}$ are independently as defined above; or
  (3) a seven-membered heterocycle
    having an otherwise unsubstituted carbon atom at the point of attachment to the rest of the compound of formula I,
    having at a first atom alpha to the point of attachment a carbon atom which is unsubstituted or substituted by an oxygen or sulphur atom,
    having at a first atom beta to the point of attachment, which atom is alpha to the foregoing first atom alpha, a carbon atom or a nitrogen atom,
    having at a second atom alpha to the point of attachment a carbon atom, which is optionally substituted by oxygen, or a nitrogen atom,
    having at a second atom beta to the point of attachment, which atom is alpha to the foregoing second atom alpha, a carbon atom or a nitrogen atom,
    and having at the two remaining atoms carbon atoms;
    a double bond may be present between the second atom alpha and the second atom beta;
    the seven-membered heterocycle may be fused to one or two aromatic rings via any adjacent pair of atoms other than the point of attachment and the first atom alpha alone or in combination;
    the aromatic ring may be benzene or a five-membered heterocycle containing 1, 2, 3 or 4 heteroatoms chosen from O, N and S providing that not more than one heteroatom is O or S or a six-membered heterocycle containing 1, 2 or 3 nitrogen atoms;
    alternatively a pair of adjacent carbon atoms in the seven-membered heterocycle, other than the point of attachment and the first atom alpha alone or in combination, may form part of a fused cyclopropyl or cyclopentyl ring;
    one to three substitutable atoms of the seven-membered heterocycle are optionally substituted by:
      an aromatic ring as defined above optionally substituted by hydroxy, halogen, methoxy or alkyl having one to four carbon atoms;
      an alkyl group having one to four carbon atoms optionally substituted by a halogen atom, hydroxy, an aromatic ring as defined above optionally substituted by hydroxy, halogen, methoxy or alkyl having one to four carbon atoms, cycloalkyl having three to seven carbon atoms, methoxy, bicycloalkyl having seven to twelve carbon atoms, heterocycle having five to seven atoms one of which is oxygen, nitrogen or sulphur which is optionally oxidized;
      a heterocycle having five to seven atoms one of which is oxygen, nitrogen or sulphur which is optionally oxidized;
      cycloalkyl having three to seven carbon atoms;
      or bicycloalkyl having seven to twelve carbon atoms;
      or the two groups A attached to the same nitrogen atom, together with that atom, form: a five-membered heterocyclic ring optionally containing 1, 2 or 3 further heteroatoms chosen from O, N and S, not more than one of the heteroatoms being O or S; or a six-membered heterocyclic ring optionally containing 1 or 2 further nitrogen atoms; each of which is optionally substituted by one to three groups independently chosen from:
    (a) halogen, cyano and nitro,
    (b) hydroxy,
    (c) $C_{1-4}$alkyl, $C_{2-4}$alkenyl and $C_{2-4}$alkynyl,
    (d) $C_{1-4}$alkoxy,
    (e) $NR^6R^7$ wherein $R^6$ and $R^7$ are independently as defined above,
    (f) $CO_2R^8$ wherein $R^8$ is independently as defined above,
    (g) $CONR^6R^7$ or $OCONR^6R^7$ wherein $R^6$ and $R^7$ are independently as defined above,
    (h) $SO_2NR^6R^7$ wherein $R^6$ and $R^7$ are independently as defined above,
    (i) $CH_2NR^6R^7$ wherein $R^6$ and $R^7$ are independently as defined above,
    (j) $N(R^8)COR^{8'}$ wherein $R^8$ is independently as defined above and $R^{8'}$ is independently as defined for $R^8$, and
    (k) $NR^8SO_2R^{8'}$ wherein $R^8$ and $R^{8'}$ are independently as defined above;

B is C=O or CHOH in the R configuration;
X is oxygen or a bond;
n is zero or one, and
p is zero, one, two or three; and
q is zero, one, two or three;
with the proviso that no carbon atom is substituted by more than one hydroxy group.

2. The compound of claim 1 or a pharmaceutically acceptable salt thereof, with the proviso that when $R^1$ is t-butyl, X is O, $R_2$ is OH, $R_3$ is benzyl, n is 1, $R_5$ is benzyl and each A is H, $R^4$ is not 2-carboxyethyl and $R_4$ is not sec-butyl.

3. The compound of claim 1 of Formula I', I" or I'":

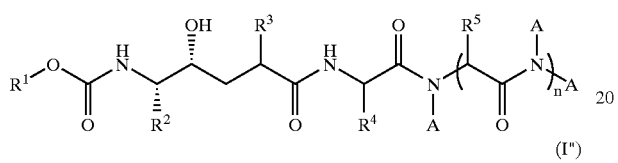
(I')

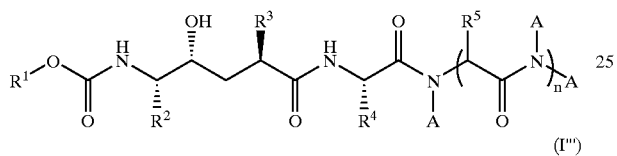
(I")

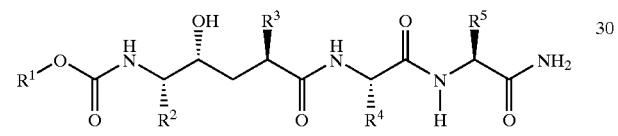
(I'")

or a pharmaceutically acceptable salt thereof.

4. The compound of claim 1 wherein:
R¹ is
(1) $C_{1-10}$alkyl, $C_{2-10}$alkenyl or $C_{2-10}$alkynyl optionally substituted with one or more substituents independently chosen from:
  (i) hydroxy;
  (ii) halogen;
  (iii) amino;
  (iv) $C_{1-4}$alkoxy; and
  (v) phenyl which is optionally substituted by one or two groups independently chosen from:
    (a) halogen, cyano and nitro,
    (b) hydroxy,
    (c) $C_{1-4}$alkyl, $C_{2-4}$alkenyl and $C_{2-4}$alkynyl,
    (d) $C_{1-4}$alkoxy and
    (e) amino; or
(2) phenyl which is optionally substituted by one or two groups independently chosen from:
  (a) halogen, cyano and nitro,
  (b) hydroxy,
  (c) $C_{1-4}$alkyl, $C_{2-4}$alkenyl and $C_{2-4}$alkynyl,
  (d) $C_{1-4}$alkoxy and
  (e) amino;

$R^2$ and $R^3$ are both $(CH_2)_pQ^1$ wherein $Q^1$ is phenyl optionally substituted by one or two groups independently chosen from:
  (a) halogen,
  (b) hydroxy,
  (c) $C_{1-4}$alkyl, $C_{2-4}$alkenyl and $C_{2-4}$alkynyl,
  (d) $C_{1-4}$alkoxy and
  (e) amino;

$R^4$ and $R^5$ are independently chosen from $C_{1-6}$alkyl optionally substituted by halogen, hydroxy, amino or $C_{1-4}$alkoxy and $(CH_2)_qQ^2$ wherein $Q^2$ is phenyl optionally substituted by hydroxy, $C_{1-4}$alkyl, $C_{1-4}$alkoxy, thiol, $C_{1-4}$alkylthio, halogen, amino, carboxy, amido, $CO_2H$ and $—NHC(NH_2)_2$;

A is hydrogen or

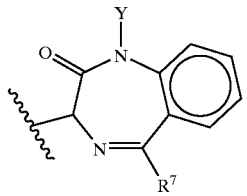

wherein $R^7$ is phenyl, $C_{1-6}$alkyl or $C_{3-7}$cycloalkyl;
Y is hydrogen or $C_{1-6}$ alkyl;
n is zero or one;
p is one; and
q is zero or one.

5. A compound selected from the group consisting of:
{1S-benzyl-4R-[1-(1S-carbamoyl-2-(R)-hydroxypropylcarbamoyl)-(S)-ethylcarbamoyl]-2R-hydroxy-5-phenylpentyl}-carbamic acid, tert-butyl ester;

{1S-benzyl-4R-[1-(1S-carbamoyl-2-(S)-methylbutylcarbamoyl)-1S-2-methylpropylcarbamoyl]-2R-hydroxy-5-phenylpentyl}-carbamic acid, tert-butyl ester;

{1S-benzyl-4-[1-(5-cyclohexyl-2-oxo-2,3-dihydro-1H-benzo[e][1,4]diazepin-3(R,S)-ylcarbamoyl)-(S)-ethylcarbamoyl]-2R-hydroxybutyl}-carbamic acid, tert-butyl ester;

{1S-benzyl-4R-[1-(5-cyclohexyl-2-oxo-2,3-dihydro-1H-benzo[e][1,4]diazepin-3(R,S)-ylcarbamoyl)-(S)-ethylcarbamoyl]-2R-hydroxy-5-phenylpentyl}-carbamic acid, tert-butyl ester;

{1S-benzyl-4R-[1-(1S-carbamoyl-2-phenylethylcarbamoyl)-1S-3-methylbutylcarbamoyl]-2R-hydroxy-5-phenylpentyl}-carbamic acid, benzyl ester;

{1S-benzyl-4R-[1-(1S-carbamoyl-2-phenylethylcarbamoyl)-1S-3-methylbutylcarbamoyl]-2-oxo-5-phenylpentyl}-carbamic acid tert-butyl ester;

{1S-benzyl-4R-[1-(1S-carbamoyl-2-phenylethylcarbamoyl)-1S-3-methylbutylcarbamoyl]-2R-hydroxy-5-phenylpentyl}carbaxnic acid tert-butyl ester;

{1S-benzyl-4R-[1-(1S-carbamoyl-2-phenylethylcarbarnoyl)-S-ethylcarbamoyl]-2R-hydroxy-5-phenylpentyl}carbamic acid tert-butyl ester;

(1S-benzyl-4R-{1S-[(carbamoylphenylmethyl)carbamoyl]-S-ethylcarbamoyl}-2R-hydroxy-5-phenylpentyl)carbamic acid tert-butyl ester;
and pharmaceutically acceptable salts thereof.

6. A compound which is:
{1S-benzyl-4R-[1-(1S-carbamoyl-2-phenylethylcarbamoyl)-1S-3-methylbutylcarbamoyl]-2R-hydroxy-5-phenylpentyl}carbamic acid tert-butyl ester;
or a pharmaceutically acceptable salt thereof.

7. A pharmaceutical composition comprising a compound of claim 1 and a pharmaceutically acceptable carrier.

8. A method for the treatment of a patient suffering from or prone to a condition associated with the deposition of β-amyloid which comprises administering to the patient an effective amount of a compound of claim 1 or a pharmaceutically acceptable salt thereof.

9. A method for the treatment of a patient suffering from or prone to Alzheimer's disease which comprises administering to the patient an effective amount of a compound of claim 1 or a pharmaceutically acceptable salt thereof.

* * * * *